United States Patent [19]

Nishiyama et al.

[11] Patent Number: 4,563,529

[45] Date of Patent: * Jan. 7, 1986

[54] PROCESS FOR PRODUCING TRIFLUOROMETHYLPYRIDINES

[75] Inventors: Ryuzo Nishiyama, Takatsuki; Kanichi Fujikawa, Moriyama; Isao Yokomichi, Moriyama; Yasuhiro Tsujii, Moriyama; Shigeyuki Nishimura, Shiga, all of Japan

[73] Assignee: Ishihara Sangyo Kaisha Ltd., Osaka, Japan

[ * ] Notice: The portion of the term of this patent subsequent to May 5, 1998 has been disclaimed.

[21] Appl. No.: 270,567

[22] Filed: Jun. 4, 1981

[30] Foreign Application Priority Data

Jun. 19, 1980 [JP] Japan .................................. 55-83147

[51] Int. Cl.$^4$ ............................................ C07D 211/72
[52] U.S. Cl. ..................... 546/345; 546/346; 570/194; 570/195; 570/196
[58] Field of Search ................ 546/346, 345; 570/195, 570/196, 194

[56] References Cited

U.S. PATENT DOCUMENTS

| | | | |
|---|---|---|---|
| 2,516,402 | 7/1950 | McBee et al. | 546/346 |
| 3,787,420 | 1/1974 | Torba | 546/300 |
| 4,288,599 | 9/1981 | Nishiyama et al. | 546/346 |

FOREIGN PATENT DOCUMENTS

| | | | |
|---|---|---|---|
| 0013474 | 7/1978 | European Pat. Off. | 546/346 |
| 0009212 | 2/1980 | European Pat. Off. | 546/346 |
| 1097673 | 1/1968 | United Kingdom | 546/346 |
| 2045245 | 10/1980 | United Kingdom | 546/346 |
| 2045761 | 11/1980 | United Kingdom | 546/346 |

OTHER PUBLICATIONS

W.O. Publication No. 79/00094, publication on Mar. 8, 1979.

*Primary Examiner*—Henry R. Jiles
*Assistant Examiner*—Robert C. Whittenbaugh
*Attorney, Agent, or Firm*—Oblon, Fisher, Spivak, McClelland & Maier

[57] ABSTRACT

A trifluoromethylpyridine selected from the group consisting of α-trifluoromethylpyridine, γ-trifluoromethylpyridine, a bis(trifluoromethyl)pyridine and chlorides thereof which have 1 to 3 chlorine atoms in its pyridine nucleus is produced by reacting a pyridine derivative selected from the group consisting of α-picoline, γ-picoline and a lutidine with chlorine and anhydrous hydrogen fluoride at a temperature of 300° to 600° C. in a vapor phase in the presence of a diluent and a catalyst comprising a fluoride of a metallic element selected from the group consisting of aluminum, chromium, iron, nickel, manganese, cobalt and copper.

7 Claims, No Drawings

PROCESS FOR PRODUCING TRIFLUOROMETHYLPYRIDINES

BACKGROUND OF THE INVENTION

1. Field of the Invention

The present invention relates to a process for producing trifluoromethylpyridines directly from α-picoline, γ-picoline and lutidines. In particular, it relates to a process for producing α or γ-trifluoromethylpyridine, bis(trifluoromethyl)pyridines or chlorides having 1 to 3 chlorine atoms in their pyridine nucleus (hereinafter referring to as trifluoromethylpyridines) which comprises reacting α-picoline, γ-picoline or lutidines (hereinafter referring to as pyridines) with chlorine and anhydrous hydrogen fluoride in the presence of diluent and special catalyst.

2. Description of the Prior Arts

The trifluoromethylpyridines are compounds useful as raw material for herbicide, insecticide and so on.

As conventional processes for producing the trifluoromethylpyridines, they have been known by U.S. Pat. Nos. 2,516,402 and 3,787,420 and WO Publication No. 79/00094 etc., however these processes are only experimental small scale.

In said U.S. Patents, there has been disclosed a process for producing the trifluoromethylpyridines which comprises (1) reacting the pyridines with chloride gas in a liquid phase under light radiation, or reacting them with chlorine gas in a vapor phase in the presence of a diluent at an elevated temperature to produce the corresponding trichloromethylpyridines and (2) reacting these trichloromethylpyridines with hydrogen fluoride in an autoclave, or an antimony trifluoride in a liquid phase. However, this chlorination step requires a long time for the reaction or produces a large quantity of by-products to be difficult to separate the object intermediates. This fluorination step requires also a long time for the reaction and a use of an autoclave or expensive antimony trifluoride. Therefore, it is not satisfactory as an industrial process.

Also, in said WO Publication, there has been disclosed a process for producing a trifluoromethylpyridine which comprises reacting a picolinic acid with sulfur tetrafluoride in the presence of hydrogen fluoride in an autoclave. However, the picolinic acid as a raw material is expensive and the sulfur tetrafluoride which is toxic to men and beasts is used. It requires also a long time for the reaction and a use of an autoclave. Therefore, it has many industrial disadvantages.

SUMMARY OF THE INVENTION

The present invention has been attained by the finding that the trifluoromethylpyridines can be obtained in a single step and for a short time by a vapor phase reaction of a pyridine with chlorine and anhydrous hydrogen fluoride in the presence of a diluent and a special catalyst.

A first object of the present invention is to provide a production of the trifluoromethylpyridine which is important raw materials for agricultural chemicals with industrial advantages.

A second object of the present invention is to produce the trifluoromethylpyridines from the pyridines directly by a single step.

A third object of the present invention is to provide a process for continuously producing said trifluoromethylpyridine for a short time by a reaction of a pyridine with chlorine and anhydrous hydrogen fluoride in a vapor phase.

The other objects of the present invention will be clear by the following description.

The foregoing and other objects of the present invention have been attained by providing a process for producing a trifluoromethylpyridine selected from the group consisting of α-trifluoromethylpyridine, γ-trifluoromethylpyridine, a bis(trifluoromethyl)pyridine and a chloride having 1 to 3 chlorine atoms in its pyridine nucleus which comprises reacting a pyridine derivative selected from the group consisting of α-picoline, γ-picoline and a lutidine with chlorine and anhydrous hydrogen fluoride at a temperature of 300° to 600° C. in a vapor phase in the presence of a diluent and a catalyst comprising a fluoride of metallic element selected from the group consisting of aluminum, chromium, iron, nickel, manganese, cobalt and copper.

DETAILED DESCRIPTION OF THE PREFERRED EMBODIMENTS

The fluoride of aluminum, chromium, iron, nickel, manganese, cobalt or copper which is used as a catalytic component in the present invention can be exemplified as follows: for example, aluminum trifluoride ($AlF_3$) as aluminum fluoride; chromium (II) fluoride ($CrF_2$), chromium (III) fluoride ($CrF_3$), chromium (IV) fluoride ($CrF_4$) as chromium fluorides; iron (II) fluoride ($FeF_2$), iron (III) fluoride ($FeF_3$) as iron fluorides; nickel (II) fluoride ($NiF_2$), nickel (III) fluoride ($NiF_3$) as nickel fluorides; manganese (II) fluoride ($MnF_2$), manganese (III) fluoride ($MnF_3$), manganese (IV) fluoride ($MnF_4$) as manganese fluoride; cobalt (II) fluoride ($CoF_2$), cobalt (III) fluoride ($CoF_3$) as cobalt fluorides; copper (I) fluoride ($CuF$), copper (II) fluoride ($CuF_2$) as copper fluorides.

One or more of the fluids can be used. Among the catalytic components, a fluoride of aluminum, chromium, iron or copper is preferably used for an industrial purpose.

An amount of the catalytic component is not critical and depending upon the reaction conditions, it is usually in range of 0.001 to 3 moles based on the pyridine as the raw material. In usual, such catalytic component is admixed with a carrier such as activated carbon and activated alumina, and the mixture is treated in a form of granules or pellets having a desired size. This catalyst can be placed as a fixed bed or fluidized bed in a gas stream which contains raw materials, a diluent and a reaction product. The catalyst can be placed by charging said metallic fluoride itself into the reaction tube. In an industrial process, it is preferable to charge the metallic oxide, chloride, hydroxide or carbonate, or a hydrate thereof and to convert it into the fluoride thereof in the reaction tube by reacting it with anhydrous hydrogen fluoride. For example, a carrier of activated alumina supporting the metallic oxide or chloride such as chromous trioxide, ferric chloride and nickel oxide is fed into the reaction tube and anhydrous hydrogen fluoride is fed at a temperature of 200° to 600° C. to convert it into said metallic fluoride. Hereafter the reaction relating to the present invention is carried out.

The diluent can be an organic solvent such as halogenated hydrocarbons such as carbon tetrachloride, chloroform, methylene chloride, F-112 ($CFCl_2.CFCl_2$) and F-113 ($CF_2Cl.CFCl_2$) and an inert gas such as nitrogen, helium and argon. The diluent has the functions for controlling a combustion, carbonization and formation of tar by-products. In the process of the present invention, a raw material and a diluent can be separately fed into the reaction tube or can be fed as a mixture thereof. They can be fed simultaneously or sequentially, or in a lump or in parts into the reaction tube. For example, a mixture of the pyridine and the diluent, or a mixture of chlorine and anhydrous hydrogen fluoride is fed separately.

Amounts of chlorine and anhydrous hydrogen fluoride are not critical and depending upon differences between a kind of the pyridine as raw material, a kind of the object product and a reaction apparatus, and in general, they are respectively in ranges of 3.5 to 15 moles and 3 to 20 moles per one mole of the pyridine as raw material. An amount of the diluent is usually in range of 3 to 70 moles per one mole of the pyridine as raw material. A reaction temperature is generally in range of 300° to 600° C., preferably 350° to 450° C. and a residence time of a reaction mixture in a reaction zone is in range of 1 to 60 seconds, preferably 1 to 40 seconds.

In usual, gaseous materials containing the fluorinated products as main component, the unreacted anhydrous hydrogen fluoride and chlorine, the intermediates, hydrogen chloride as a by-product and the diluent are discharged from the reaction tube. The trifluoromethylpyridines are obtained as a liquid mixture through a desired cooling and condensing device. In the liquid mixture, there are contained the following materials; for example, when α-picoline is used as raw material, there are contained α-trifluoromethylpyridine and its chlorides such as 6-chloro, 4,6-dichloro, 3,6-dichloro and 3,5,6-trichloro-2-trifluoromethylpyridines; when γ-picoline is used as raw material, there are contained 4-trimethylpyridine and its chlorides such as 2-chloro and 2,6-dichloro-4-trifluoromethylpyridines; when a lutidine is used as raw material, since such lutidine itself has forms of isomers of 2,4-lutidine, 2,5-lutidine, 2,6-lutidine and 3,5-lutidine, the reaction products are depending upon a kind of lutidine. When 2,4-lutidine is used as raw material, there are contained 2,4-bis(trifluoromethyl)pyridine and its chlorides such as 6-chloro, 5,6-dichloro, and 3,5,6-trichloro-2,4-bis(trifluoromethyl)pyridines; when 3,5-lutidine is used as raw material, there are contained 3,5-bis(trifluoromethyl)pyridine and its chlorides such as 2-chloro, 2,6-dichloro and 2,4,6-trichloro-3,5-bis(trifluoromethyl)pyridines; when 2,6-lutidine is used as raw material, there are contained 2,6-bis(trifluoromethyl)pyridine and its chlorides such as 4-chloro, 3,4-dichloro and 3,4,5-trichloro-2,6-bis(trifluoromethyl)pyridines.

In accordance with the process of the present invention, the trifluoromethylpyridines are obtained, for example, at the yield of higher than 75%. When the intermediates which are not converted into the object trifluoromethylpyridines are remained in a liquid mixture, these intermediates can be recycled to the reaction zone after separating and recovering them with the unreacted raw material or the diluent. Further the trifluoromethylpyridines can be purified by conventional purifying treatments such as an extraction, a distillation and a crystallization whereby a single compound of for example, 6-chloro-2-trifluoromethylpyridine, 2-chloro-4-trifluoromethylpyridine, 6-chloro-2,4-bis(trifluoromethyl)pyridine or 2,6-dichloro-3,5-bis(trifluoromethyl)pyridine can be obtained at the high yield.

The present invention will be further illustrated by certain examples, however, the scope of the present invention is not limited by any descriptions.

EXAMPLE 1

A vertical reactor made of Inconel which contained a reaction zone having an inner diameter of 80 mm and a height of 1000 mm and a catalyst fluidized bed having the catalyst packing part of 500 mm in height from the bottom was used as a reactor. Two preheating tubes made of Inconel having an inner diameter of 20 mm and a length of 1500 mm were connected to the bottom of the reactor. The reaction tube and preheating tubes were covered outwardly by each electric heater and insulator so as to control the temperature.

Trihydrates of chromous trifluoride supported by activated alumina having granular diameter of 32 to 200 mesh at a ratio of 81 to 1000 by weight (1740 g.), was fluorinated and was charged into the catalyst packing part, and the reactor was heated at a temperature of 380° to 400° C. Through one preheating tube, a mixture of α-picoline and nitrogen gas was fed into the reactor at a rate of 250 g./hour of α-picoline and at a molar ratio of nitrogen to α-picoline of 5 and through another preheating tube, a mixture of anhydrous hydrogen fluoride and chlorine gas was fed into the reactor at a molar ratio of anhydrous hydrogen fluoride to α-picoline of 5 and a molar ratio of chlorine gas to α-picoline of 4 to react them for 2 hours.

The residence time of the reaction mixture in the reaction zone was about 8 seconds.

The gas discharged from the reactor was obtained by passing it through a cooling condenser and a water washing tower. The reaction mixture was neutralized with ammonia water and was treated by a steam distillation to produce 730 g. of an oily product.

The oily product was analyzed by a gas chromatography with a temperature programmer to find that the oily product contained 14.9% of 2-trifluoromethylpyridine, 48.3% of 6-chloro-2-trifluoromethylpyridine, 4.0% of 4,6-dichloro-2-trifluoromethylpyridine and 32.8% of chloro 2-perchlorofluoromethylpyridine. The oily product was treated by conventional refining and recrystallizing means to obtain 246 g. of 6-chloro-2-trifluoromethylpyridine.

EXAMPLE 2

The same reactor as used in Example 1 was used. As the catalyst, after fluorinating ferric chloride supported by activated alumina having granular diameter of 32 to 200 mesh at the ratio of 81 to 1000 by weight (1510 g.), the treated material was charged into the catalyst packing part. In accordance with the process of Example 1 except feeding γ-picoline at a rate of 265 g. per hour, a reaction was carried out for 3 hours to obtain 1122 g. of an oily product.

The oily product was analyzed by the same gas chromatography used in Example 1 to find that the oily product contained 16.6% of 4-trifluoromethylpyridine, 45.8% of 2-chloro-4-trifluoromethylpyridine, 1.3% of 3-chloro-4-trifluoromethylpyridine, 19.2% of 2,6-dichloro-4-trifluoromethylpyridine and 17.1% of chloro 4-perchlorofluoromethylpyridine. The oily product was washed with hydrochloric acid and treated in accordance with the process of Example 1 to obtain 349 g. of 2-chloro-4-trifluoromethylpyridine.

EXAMPLE 3

The same reactor as used in Example 1 was used and the same catalyst as used in Example 2 was charged into the catalyst packing part. In accordance with the process of Example 2 except feeding 250 g. per hour of γ-picoline and chlorine gas of 6 times moles as much as it, a reaction was carried out at 400° to 420° C. for one hour to obtain 441 g. of an oily product.

The oily product was analyzed by said gas chromatography to find that the oily product contained 1.0% of 4-trifluoromethylpyridine, 2.0% of 2-chloro-4-trifluoromethylpyridine, 72.3% of 2,6-dichloro-4-trifluoromethylpyridine, 7.4% of 2,3,6-trichloro-4-trifluoromethylpyridine and 17.3% of chlor 4-perchlorofluoromethylpyridine. The oily product was treated in accordance with the process of Example 1 to obtain 197 g. of 2,6-dichloro-4-trifluoromethylpyridine.

EXAMPLE 4

The same reactor as used in Example 1 was used, and 1500 g. of aluminum trifluoride having granular diameter of 60 to 250 mesh was charged into the catalyst packing part.

The reactor was heated at 400° to 420° C. Through one preheating tube, a mixture of 2,4-lutidine and nitrogen gas was fed into the reactor at a rate of 115 g. per hour of 2,4-lutidine and at a molar ratio of nitrogen gas to the lutidine of 7 and through another preheating tube, a mixture of anhydrous hydrogen fluoride and chlorine gas was fed into the reactor at a molar ratio of anhydrous hydrogen fluoride to lutidine of 10 and at a molar ratio of chlorine gas to lutidine of 8 to react them for about 3.5 hours. The residence time of the reaction mixture in the reaction zone was about 11 seconds.

In accordance with the process of Example 1, the gas discharged from the reactor was treated to obtain 253 g. of 6-chloro-2,4-bis(trifluoromethyl)pyridine.

EXAMPLE 5

The same reactor as used in Example 1 was used. As the catalyst, 130 g. of ferric chloride supported by 1740 g. of activated carbon having granular diameter of 105 to 210 mesh was charged into the catalyst packing part and treated by feeding anhydrous hydrogen fluoride at a rate of 1.0N liter/min. at 200° C. for one hour to prepare the catalyst.

The reactor was heated at 420° C. Through one preheating tube, a mixture α-picoline and nitrogen gas was fed into the reactor at a rate of 200 g. of α-picoline per hour and at a molar ratio of nitrogen gas to α-picoline of 5 and through another preheating tube, a mixture of anhydrous hydrogen fluoride and chlorine gas was fed into the reactor at a molar ratio of anhydrous hydrogen fluoride to α-picoline of 7 and at a molar ratio of chlorine gas to α-picoline of 5 to react them for 5 hours. The residence time of the reaction mixture in the reaction zone was about 8.2 seconds.

In accordance with the process of Example 1, the gas discharged from the reactor was treated to obtain 2340 g. of an oily product. The oily product was analyzed by said gas chromatography to find that the oily product contained 11.8% of 2-trifluoromethylpyridine, 39.6% of 6-chloro-2-trifluoromethylpyridine, 3.2% of 4,6-dichloro-2-trifluoromethylpyridine and 45.4% of chloro 2-perchlorofluoromethylpyridine. The oily product was treated in accordance with the process of Example 1 to obtain 550 g. of 6-chloro-2-trifluoromethylpyridine.

EXAMPLES 6 to 10

In accordance with the process of Example 5 except using chromium trichloride, nickel dichloride, cobalt dichloride, manganese dichloride or copper dichloride, instead of ferric chloride each reaction and each post treatment were carried out to obtain each oily product shown in Table 1.

TABLE 1

| Example No. | Catalyst | Content (%) | | | |
|---|---|---|---|---|---|
| | | $2\text{-}CF_3-$ pyridine | $6\text{-}Cl-2\text{-}CF_3-$ pyridine | $4,6\text{-}Cl_2\text{-}2\text{-}CF_3-$pyridine | Chloro 2-perchlorofluoromethylpyridine |
| 6 | $CrF_3$ | 9.6 | 40.2 | 4.2 | 46.0 |
| 7 | $NiF_2$ | 10.8 | 38.6 | 2.4 | 48.2 |
| 8 | $CoF_2$ | 11.2 | 37.4 | 2.6 | 48.8 |
| 9 | $MnF_2$ | 8.6 | 39.4 | 3.1 | 48.9 |
| 10 | $CuF_2$ | 10.6 | 41.2 | 4.6 | 43.6 |

EXAMPLE 11

A vertical reactor made of Inconel which contained a reaction zone having an inner diameter of 100 mm and a height of 2300 mm and a catalyst fluidized bed having the catalyst packing part of 800 mm in height from the bottom was used as reactor. Two preheating tubes made of Inconel having an inner diameter of 50 mm and a length of 500 mm were connected to the bottom of the reactor. The reaction tube and preheating tubes were covered outwardly by each electric heater and insulator so as to control the temperature.

After fluorinating hexahydrate of nickel dichloride supported by aluminum trifluoride having granular diameter of 105 to 255μ at the ratio of 44 to 1000 by weight (3800 g.), the treated material was charged into the catalyst packing part, and the reactor was heated at a temperature of 340° to 400° C.

Through one preheating tube, a mixture of γ-picoline and nitrogen gas was fed into the reactor at a rate of 250 g. of γ-picoline per hour and at a molar ratio of nitrogen gas to γ-picoline of 5 and through another preheating tube, a mixture of anhydrous hydrogen fluoride and chlorine gas was fed into the reactor at a molar ratio of anhydrous hydrogen fluoride to γ-picoline of 5 and at a molar ratio of chlorine gas to γ-picoline of 5 to react them for 6 hours. The residence time of the reaction mixture in the reaction zone was about 27 to 30 seconds.

The gas discharged from the reactor was treated in accordance with the process of Example 1 to obtain 2400 g. of oily product. The oily product was analyzed by said gas chromatography to find that the oil contained 18.1% of 4-trifluoromethylpyridine, 44.6% of 2-chloro-4-trifluoromethylpyridine, 2.6% of 3-chloro-4-trifluoromethylpyridine, 10.8% of 2,6-dichloro-4-trifluoromethylpyridine, and 23.9% of chloro 4-perchlorofluoromethylpyridine. The oily product was treated in accordance with the process of Example 2 to obtain 720 g. of 2-chloro-4-trifluoromethylpyridine.

EXAMPLES 12 to 14

In accordance with the processes of Example 11 except using cobalt dichloride, manganese dichloride and copper dichloride, instead of nickel dichloride, a reaction and a post treatment were carried out to obtain each oily product shown in Table 2.

TABLE 2

| Example No. | Catalyst | Content (%) | | | | |
|---|---|---|---|---|---|---|
| | | 4-CF$_3$—pyridine | 2-Cl—4-CF$_3$—pyridine | 3-Cl—4-CF$_3$—pyridine | 2,6-Cl$_2$—4-CF$_3$—pyridine | Chloro 4-perchlorofluoromethylpyridine |
| 12 | CoF$_2$/AlF$_3$ | 16.1 | 43.2 | 3.6 | 8.8 | 28.3 |
| 13 | MnF$_2$/AlF$_3$ | 17.1 | 45.6 | 2.2 | 11.6 | 23.5 |
| 14 | CuF$_2$/AlF$_3$ | 19.2 | 47.6 | 2.8 | 16.2 | 14.2 |

EXAMPLE 15

The same reactor as used in Example 1 was used. The material treated by fluorinating copper dichloride supported by aluminum trifluoride having granular diameter of 105 to 255µ at the ratio of 67 to 1000 by weight was charged into the catalyst packing part.

The reactor was heated at 420° C., through one preheating tube, a mixture of 3,5-lutidine and nitrogen gas was fed at a rate of 140 g. of the lutidine per hour and at a molar ratio of nitrogen gas to the lutidine of 6, and through another preheating tube, a mixture of anhydrous hydrogen fluoride and chlorine gas was fed at a molar ratio of anhydrous hydrogen fluoride to the lutidine of 10 and at a molar ratio of chlorine gas to the lutidine of 8 into the reactor, and the reaction was carried out for 2 hours. The residence time of the reaction mixture in the reaction zone was about 10 seconds.

In accordance with the process of Example 1, a post treatment was carried out to obtain 390 g. of 2-chloro-3,5-bis(trifluoromethyl)pyridine.

EXAMPLE 16

The same reactor as used in Example 1 was used. Aluminum trifluoride having granular diameter of 105 to 255µ supporting components of 66.3 g. of NiCl$_2$.6H$_2$O, 60 g. of CrO$_3$, 7.5 g. of FeCl$_3$ and 8.7 g. of MnCl$_2$ at the ratio of 1000 to 100 was fluorinated at 250° C. with anhydrous hydrogen fluoride to prepare a catalyst, and 1500 g. of the treated catalyst was used.

The reactor was heated at 370° C., a mixture of α-picoline, and nitrogen gas (at a rate of 200 g. of α-picoline per hour and at a molar ratio of nitrogen gas to picoline of 5), and a mixture of chlorine gas and anhydrous hydrogen fluoride (at each molar ratio of chlorine gas or anhydrous hydrogen fluoride to picoline of 5) were respectively fed into the reactor to react them for 5 hours at the residence time of about 9.7 seconds.

In accordance with the process of Example 1 a gas discharged from the reactor was treated to obtain 1700 g. of an oily product. The oily product was analyzed by said gas chromatography to find that the oily product contained 10.6% of 2-trifluoromethylpyridine, 51.4% of 6-chloro-2-trifluoromethylpyridine, 6.5% of 4,6-dichloro-2-trifluoromethylpyridine and 31.5% of chloro 2-perchlorofluoromethylpyridine. The oily product was treated to obtain 590 g. of 6-chloro-2-trifluoromethylpyridine.

We claim:

1. A process for producing a trifluoromethylpyridine selected from the group consisting of α-trifluoromethylpyridine, γ-trifluoromethylpyridine, bis(trifluoromethyl)pyridines and chloro derivatives thereof which have 1 to 3 chlorine atoms attached to the pyridine nucleus comprising reacting a pyridine derivative selected from the group consisting of α-picoline, γ-picoline and dimethylpyridines with chlorine and anhydrous hydrogen fluoride at a temperature of 300° to 600° C. in a vapor phase reaction in the presence of a diluent and a catalyst comprising a fluoride of a metallic element selected from the group consisting of aluminum, chromium, iron, nickel, manganese, cobalt and copper.

2. The process according to claim 1, wherein the residence time of the reaction mixture in the reaction zone is from 1 to 60 seconds.

3. The process according to claim 2, wherein said residence time is 1 to 40 seconds.

4. The process according to claim 1, wherein said pyridine derivative is α-picoline and said trifluoromethylpyridine is 2-trifluoromethylpyridine, 6-chloro-2-trifluoromethylpyridine, or 4,6-dichloro-2-trifluoromethylpyridine.

5. The process according to claim 1, wherein said pyridine derivative is γ-picoline and said trifluoromethylpyridine is 4-trifluoromethylpyridine, 2-chloro-4-trifluoromethylpyridine, or 2,6-dichloro-4-trifluoromethylpyridine.

6. The process according to claim 1 wherein said reaction is carried out at a temperature of 350° to 450° C.

7. The process according to claim 1 wherein said catalyst is a fluoride of aluminum, chromium, iron or copper.

* * * * *